(12) United States Patent
Vitello et al.

(10) Patent No.: US 11,357,588 B1
(45) Date of Patent: Jun. 14, 2022

(54) NEEDLE PACKAGING AND DISPOSAL ASSEMBLY

(71) Applicants: Patrick Vitello, Pompano Beach, FL (US); Jonathan Vitello, Ft. Lauderdale, FL (US); Peter Lehel, Boca Raton, FL (US)

(72) Inventors: Patrick Vitello, Pompano Beach, FL (US); Jonathan Vitello, Ft. Lauderdale, FL (US); Peter Lehel, Boca Raton, FL (US)

( * ) Notice: Subject to any disclaimer, the term of this patent is extended or adjusted under 35 U.S.C. 154(b) by 0 days.

(21) Appl. No.: 17/104,807

(22) Filed: Nov. 25, 2020

Related U.S. Application Data (60) Provisional application No. 62/939,958, filed on Nov. 25, 2019.

(51) Int. Cl.
*A61B 50/36* (2016.01)
*B65D 75/36* (2006.01)

(52) U.S. Cl.
CPC .......... *A61B 50/362* (2016.02); *B65D 75/366* (2013.01)

(58) Field of Classification Search
CPC ............................ A61B 50/362; B65D 75/366
USPC ........................................................ 206/365
See application file for complete search history.

(56) References Cited

U.S. PATENT DOCUMENTS

| | | | |
|---|---|---|---|
| 722,943 A * | 3/1903 | Chappell | B65D 77/245 206/229 |
| 732,662 A | 6/1903 | Smith | |
| 1,678,991 A | 7/1928 | Marschalek | |
| 1,970,631 A | 8/1934 | Sherman | |
| 2,477,598 A | 8/1949 | Hain | |
| 2,739,590 A | 3/1956 | Yochem | |
| 2,823,674 A | 2/1958 | Yochem | |
| 2,834,346 A | 5/1958 | Adams | |
| 2,875,761 A | 3/1959 | Helmer et al. | |
| 2,888,015 A | 5/1959 | Hunt | |
| 2,952,255 A | 9/1960 | Hein, Jr. | |
| 3,122,280 A | 2/1964 | Goda | |

(Continued)

FOREIGN PATENT DOCUMENTS

| | | |
|---|---|---|
| EP | 0148116 | 7/1985 |
| GB | 486367 | 6/1938 |

(Continued)

*Primary Examiner* — Jacob K Ackun
(74) *Attorney, Agent, or Firm* — Malloy & Malloy, PL; Jennie S. Malloy; Peter A. Matos (57) ABSTRACT

An assembly, for packaging and safely disposing of a needle structure, including a housing having at least one containment structure. The containment structure includes a hinge movably interconnecting a base and a needle retaining segment, between open and closed orientations. The retaining segment includes a compartment removably containing the needle structure therein and the base includes a chamber for reception of the compartment and medical needle therein, when in the closed orientation. The hinge normally biases the retaining segment and compartment outwardly at substantially a predetermined angular orientation relative to said base, in the open orientation, to facilitate access to the medical needle through an access opening in the compartment. A closure is fixedly connected to and movable with both the base and the retaining segment and is structured to removably secure said housing in said closed orientation.

15 Claims, 4 Drawing Sheets

(56) References Cited

U.S. PATENT DOCUMENTS

| | | |
|---|---|---|
| 3,245,567 A | 4/1966 | Knight |
| 3,323,798 A | 6/1967 | Miller |
| 3,364,890 A | 1/1968 | Andersen |
| 3,368,673 A | 2/1968 | Johnson |
| 3,574,306 A * | 4/1971 | Alden ............... A61M 25/02 604/162 |
| 3,598,120 A | 8/1971 | Mass |
| 3,610,241 A | 10/1971 | LeMarie |
| 3,700,215 A | 10/1972 | Hardman et al. |
| 3,706,307 A | 12/1972 | Hasson |
| 3,712,749 A | 1/1973 | Roberts |
| 3,747,751 A | 7/1973 | Miller et al. |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 3,987,930 A | 10/1976 | Fuson |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| 4,482,071 A | 11/1984 | Ishiwatari |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klien et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,742,910 A * | 5/1988 | Staebler ............... A61M 5/3213 206/365 |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,024,323 A * | 6/1991 | Bolton ............... A61B 17/0493 206/365 |
| 5,049,129 A | 9/1991 | Zdeb et al. |
| D323,392 S | 1/1992 | Bryne |
| 5,085,332 A | 2/1992 | Gettig et al. |
| 5,090,564 A * | 2/1992 | Chimienti ............ A61M 5/3205 206/365 |
| 5,135,496 A | 8/1992 | Vetter et al. |
| 5,163,922 A | 11/1992 | McElveen, Jr. et al. |
| 5,165,560 A | 11/1992 | Ennis, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,370,226 A * | 12/1994 | Gollobin ............... A61M 5/3216 206/365 |
| 5,380,295 A | 1/1995 | Vacca |
| 5,402,887 A * | 4/1995 | Shillington ......... A61M 5/3205 206/366 |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,617,954 A | 4/1997 | Kato et al. |
| 5,624,402 A | 4/1997 | Imbert |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Liff et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| 5,829,589 A | 11/1998 | Nguyen et al. |
| D402,766 S | 12/1998 | Smith et al. |
| 5,883,806 A | 3/1999 | Meador et al. |
| 5,884,457 A | 3/1999 | Ortiz et al. |
| 5,902,269 A | 5/1999 | Jentzen |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,957,314 A | 9/1999 | Nishida et al. |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsals |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,235,376 B1 | 5/2001 | Miyazaki et al. |
| 6,279,746 B1 * | 8/2001 | Hussaini ............... B65D 75/366 206/461 |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,358,241 B1 * | 3/2002 | Shapeton ............... A61B 18/14 206/365 |
| 6,375,640 B1 | 4/2002 | Teraoka |
| 6,394,983 B1 | 5/2002 | Mayoral et al. |
| 6,439,276 B1 * | 8/2002 | Wood ............... A61M 5/1782 141/27 |
| 6,485,460 B2 | 11/2002 | Eakins et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanly et al. |

(56) References Cited

U.S. PATENT DOCUMENTS

| | | |
|---|---|---|
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,036,661 B2 * | 5/2006 | Anthony ............ A61B 50/3001 206/363 |
| 7,055,273 B2 | 6/2006 | Roshkoff |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Anderasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| 7,482,166 B2 | 1/2009 | Nollert et al. |
| 7,497,330 B2 * | 3/2009 | Anthony ............ A61B 50/3001 206/363 |
| 7,503,453 B2 | 3/2009 | Cronin et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,918,830 B2 | 4/2011 | Langan et al. |
| 7,922,213 B2 | 4/2011 | Werth |
| 8,034,041 B2 | 10/2011 | Domkowski et al. |
| 8,079,518 B2 | 12/2011 | Turner et al. |
| 8,091,727 B2 | 1/2012 | Domkowwski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,413,811 B1 * | 4/2013 | Arendt ................ A61C 8/0087 206/368 |
| 8,443,999 B1 | 5/2013 | Reinders |
| D684,057 S | 6/2013 | Kwon |
| 8,512,277 B2 | 8/2013 | Del Vecchio |
| 8,528,757 B2 | 9/2013 | Bisio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,016,473 B2 | 4/2015 | Tamarindo |
| 9,082,157 B2 | 7/2015 | Gibson |
| 9,101,534 B2 | 8/2015 | Bochenko |
| D738,495 S | 9/2015 | Strong et al. |
| D743,019 S | 11/2015 | Schultz |
| 9,199,042 B2 | 12/2015 | Farrar et al. |
| 9,199,749 B1 | 12/2015 | Vitello et al. |
| 9,220,486 B2 | 12/2015 | Schweiss et al. |
| 9,220,577 B2 | 12/2015 | Jessop et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Ingram et al. |
| D777,903 S | 1/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| 9,987,438 B2 | 6/2018 | Stillson |
| D825,746 S | 8/2018 | Davis et al. |
| 10,039,913 B2 | 8/2018 | Yeh et al. |
| D831,201 S | 10/2018 | Holtz et al. |
| D834,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,315,808 B1 | 6/2019 | Taylor et al. |
| 10,376,655 B2 | 8/2019 | Pupke et al. |
| D859,125 S | 9/2019 | Weagle et al. |
| 10,758,684 B1 | 9/2020 | Vitello et al. |
| 10,773,067 B2 | 9/2020 | Davis et al. |
| 10,888,672 B1 | 1/2021 | Vitello |
| 10,898,659 B1 | 1/2021 | Vitello et al. |
| 10,912,898 B1 | 2/2021 | Vitello et al. |
| 10,933,202 B1 | 3/2021 | Banik |
| 10,953,162 B1 | 3/2021 | Hunt et al. |
| 11,040,149 B1 | 6/2021 | Banik |
| 11,040,154 B1 | 6/2021 | Vitello et al. |
| 11,097,071 B1 | 8/2021 | Hunt et al. |
| 2001/0034506 A1 | 10/2001 | Hirschman et al. |
| 2001/0056258 A1 | 12/2001 | Evans |
| 2002/0007147 A1 | 1/2002 | Capes et al. |
| 2002/0023409 A1 | 2/2002 | Py |
| 2002/0046962 A1 * | 4/2002 | Vallans ................ A61B 50/362 206/366 |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0104770 A1 * | 8/2002 | Shapeton ........... A61B 18/1402 206/363 |
| 2002/0133119 A1 | 9/2002 | Eakins et al. |
| 2003/0055685 A1 | 3/2003 | Cobb et al. |
| 2003/0146617 A1 | 8/2003 | Franko, Sr. |

(56) References Cited

U.S. PATENT DOCUMENTS

| | | |
|---|---|---|
| 2003/0183547 A1 | 10/2003 | Heyman |
| 2004/0008123 A1 | 1/2004 | Carrender et al. |
| 2004/0064095 A1 | 4/2004 | Vitello |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 | 4/2008 | Buehler et al. |
| 2008/0106388 A1 | 5/2008 | Knight |
| 2008/0140020 A1 | 6/2008 | Shirley |
| 2008/0243088 A1 | 10/2008 | Evans |
| 2008/0303267 A1 | 12/2008 | Schnell et al. |
| 2008/0306443 A1 | 12/2008 | Neer |
| 2009/0084804 A1 | 4/2009 | Caspary et al. |
| 2009/0099552 A1 | 4/2009 | Levy et al. |
| 2009/0149815 A1 | 6/2009 | Kiel et al. |
| 2009/0166311 A1 | 7/2009 | Claessens |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin et al. |
| 2014/0353196 A1 | 12/2014 | Key |
| 2015/0182686 A1 | 7/2015 | Okihara |
| 2015/0191633 A1 | 7/2015 | De Boer et al. |
| 2015/0302232 A1 | 10/2015 | Strassburger et al. |
| 2015/0305982 A1 | 10/2015 | Bochenko |
| 2015/0310771 A1 | 10/2015 | Atkinson et al. |
| 2016/0067422 A1 | 3/2016 | Davis et al. |
| 2016/0090456 A1 | 3/2016 | Ishimaru et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Viitello et al. |
| 2016/0250420 A1 | 9/2016 | Maritan et al. |
| 2016/0279032 A1 | 9/2016 | Davis |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0225843 A1 | 8/2017 | Glaser et al. |
| 2017/0239141 A1 | 8/2017 | Davis et al. |
| 2017/0319438 A1 | 11/2017 | Davis et al. |
| 2017/0354792 A1 | 12/2017 | Ward |
| 2018/0001540 A1 | 1/2018 | Byun |
| 2018/0014998 A1 | 1/2018 | Yuki et al. |
| 2018/0078684 A1 | 3/2018 | Peng et al. |
| 2018/0089593 A1 | 3/2018 | Patel et al. |
| 2018/0098915 A1 | 4/2018 | Rajagopal et al. |

FOREIGN PATENT DOCUMENTS

| | | |
|---|---|---|
| WO | WO2008000279 | 1/2008 |
| WO | WO2017086607 | 5/2015 |

\* cited by examiner

NEEDLE PACKAGING AND DISPOSAL ASSEMBLY

This patent application claims priority to U.S. Provisional patent application, namely, that having Ser. No. 62/939,958 and a filing date of Nov. 25, 2019, with the contents of this prior application being incorporated herein by reference in their entirety.

BACKGROUND OF THE INVENTION

Field of the Invention

The present invention is directed to a package assembly for at least one needle structure, operative to provide access thereto when in an open orientation and structured to accomplish safe disposal of the needle, subsequent to use, when in a closed orientation.

Description of the Related Art

In numerous medical care facilities, it is common practice to administer various medications to a patient either orally or by injection. As a result, a number of syringes, IV bags, medication carrying containers, etc. may be pre-loaded within or supplied to a medical care facility, and subsequently stored at different locations and/or stations throughout the facility. For example, at some large medical facilities, preloaded syringes or other administering containers may be delivered to multiple nurses' stations. Because of the remote location of many nurse's stations, however, a preloaded syringe is often given to other personnel for delivery to a patient's room and/or for subsequent dosing of the patient by a duly qualified nurse or other medically trained person. Also, in the case of a very expensive drug or an addictive type drug such as, but not limited to morphine, there is a danger that the pre-loaded container will be tampered with at some point, by a person seeking to improperly gain unauthorized access to the drug. This possibility can present real danger when unauthorized access to the contents of the preloaded syringe, IV bag or other container is accomplished. One possible outcome of such a situation includes the inappropriate substitution of some other, unauthorized material in the syringe or container. By way of an example only, if saline solution were substituted for a dose of morphine, this could have serious consequences. Thus, there is a problem of determining if a sealed, preloaded medication container has, or has not, been exposed to contamination or might otherwise have been compromised by it being tampered with.

However, certain problems remain in the relevant field of art. By way of example, during sterile compounding, hospital pharmacists and other compounding operators need to use various needles to fill, extract from or filter in containers while maintaining an aseptic technique. Since needles of the type referred to come in sterile packaging, usually in blister packaging with a guard or sleeve to prevent users from potential puncture hazards, such packaging frequently requires the packaging to be opened and removed from the needle, in order to make the needle readily available for sterile preparation and/or use. Once the filling or other procedure involving the needle is complete, a user must maintain the aseptic technique while trying to replace the needle guard, frequently having to use only one hand. This creates a challenge and potentially dangerous situation, while at the same time adding time delay to the overall process.

Therefore, there is a need in this area for an improved assembly or structure preferably in the form of a packaging and disposal assembly or structure, which is capable of maintaining safe, sterile conditions of various types of needles, such as those used in medical procedures of the type set forth herein. Moreover, the structural and operative features of any such improved and proposed assembly for overcoming the disadvantages set forth herein, should allow for a preferred positioning of the needle, once the packaging and disposing assembly has been opened. If any such assembly were developed, it would preferably allow for positioning of the needle to facilitate its access, whether on a single use or a repetitive use basis. Further, it would be preferable if subsequent to use, the needle could be reinserted within interior portions of the packaging and disposing assembly, and thereafter disposed and maintained in a closed orientation. The goal of any such assembly would be for the needle and the packaging and disposal assembly, once in the aforementioned closed orientation, to all be discarded without fear of puncture, contamination, etc.

Further, if any such proposed and improved packaging and disposing assembly were developed, it would also be ideal if it could be formed of an appropriate plastic material which is low in cost, relatively easy to utilize during a manufacturing process and yet sufficiently durable to facilitate reliable and efficient storage and disposal of a needle structure respectively, before and after use.

SUMMARY OF THE INVENTION

The present invention is directed to a package assembly for a needle structure such as, but not limited to, a medical needle of the type which may be associated with a syringe or other type of medical container, instrument or device. In addition, the operative structuring of the package assembly facilitates the safe disposal of the needle, subsequent to its use. As set forth in greater detail hereinafter, other advantageous features of the present invention include the disposition of the contained needle in a position which facilitates repeated or singular access thereto, when the needle is being utilized.

In more specific terms, the package assembly of the present invention comprises a housing including at least one, but possibly a plurality of containment structures. Each of the containment structures is dimensioned and configured to removably contain a needle, of the type described herein. Further, each of the one or more containment structures comprises a base and a needle retaining segment movably interconnected to one another by a hinge. The hinge is integrally or fixedly attached to a correspondingly positioned longitudinal end of each of the base and retaining segment, thereby at least partially defining a substantially clamshell configuration of the housing. As such, the hinge is oriented in transverse relation and/or substantially perpendicular to the length of the containment structure, specifically including cooperatively positioned ones of the base and retaining segment. The hinge is disposed and structured to facilitate selective positioning of corresponding ones of the base and retaining segment into and between a closed orientation and an open orientation.

In at least one additional embodiment, wherein the housing includes a plurality of containment structures, the aforementioned hinge may be common to each of the containment structures. In the alternative, each of a plurality of operatively independent hinges or hinge segments may be associated with different ones of each of the plurality of containment structures. Moreover, in each of the structurally modified embodiments of the hinge and/or hinge segments, the base and the retaining segment of each containment structure may be independently or concurrently disposed in and between the closed orientation and the open orientation.

As indicated, the hinge may be integrally or otherwise fixedly secured to corresponding longitudinal ends of each of the base and retaining segment. Accordingly, the hinge may be more specifically defined as a "living hinge" formed of the same or other appropriate material from which the housing and one or more containment structures are formed. For purposes of clarification, a living hinge is a type of hinge made of a thin flexible material, typically plastic, wherein the plastic material may vary dependent, at least in part, on the intended use of the hinged components. Advantages of using a living hinge is the ability to be continuously and repeatedly bent and/or flexed without breaking or damage. This is due, at least in part, to the creation of at least minimal friction during the operative flexing of a living hinge. Further, recognized advantages of the living hinge include a thin design requiring minimal space for the intended use, as well as the ability to be effectively used in moist or other environments where other type hinges may demonstrate wear, damage, corrosion, etc. Also, the living hinge is quiet and inexpensive, thereby facilitating its reliable use in a variety of different practical applications. However, it should be noted that hinge structures and designs, other than a living hinge may be utilized in the movable interconnection of the base and retaining segment of each of the one or more containment structures of the packaging and disposing assembly or structure of the present invention.

Yet additional structural details of the present invention include the needle retaining segment of each of the one or more containment structures comprising a compartment dimensioned and structured to retain at least one needle therein. The compartment includes an elongated configuration having a hollow interior extending along at least a majority of the length thereof and an access opening disposed in direct communication with the hollow interior. Further, the access opening is formed on and at least partially defines a one longitudinal end of the compartment disposed in substantially opposing relation to the location of the aforementioned hinge. When the base and retaining segment of the one or more containment structures are disposed in the aforementioned open orientation, the access opening, as well as the needle contained within the corresponding compartment, is readily accessible.

Accordingly, accessibility to the contained needle within the compartment via the access opening is yet another feature of the packaging and disposing assembly of the present invention. Such accessibility is further enhanced by the structuring of the corresponding hinge to maintain a predetermined angular orientation of the retaining segment and integrated compartment, upwardly and outwardly from the base of the same containment structure. Moreover, a preferred predetermined angular orientation of the retaining segment, compartment and contained needle may be defined as an acute angle. As practically utilized, the base of a given containment structure, when in an open orientation, may be disposed on a substantially horizontal supporting surface. In cooperation therewith, the retaining segment, compartment and contained needle will be disposed outwardly and/or upwardly therefrom into the aforementioned predetermined angle, such as but not limited to, an acute angle.

Therefore, the structuring of the hinge associated with a given containment structure is intended to normally bias the retaining segment into the predetermined angular relation to the base, to at least partially define the open orientation. It is also to be noted that such a predetermined angular orientation of the retaining segment, outwardly from the corresponding base will be substantially maintained, whether the needle remains in the compartment or is removed therefrom through the access opening. As will be explained in greater detail hereinafter, such a preferred, predetermined angular disposition of the retaining segment and the needle retained within the compartment, serves to position the needle for easy and possibly repetitious removal from and reinsertion within the compartment, during the utilization of the needle in the intended manner. Yet additional features of the needle packaging and disposing assembly of the present invention includes the base comprising a chamber having a hollow interior extending along at least a majority of the length of the base. The chamber includes an open, inner longitudinal side extending along at least a majority of the length of the base. The open, inner longitudinal side is disposed, dimensioned and configured to receive the compartment of the needle retaining segment therein concurrent to a closed orientation. As such, the length as well as the interior dimension of the chamber is sufficient to enclose the compartment of the corresponding retaining segment, concurrent to the compartment passing through the open longitudinal side of the chamber as the containment structure moves into the closed orientation. Moreover, when in the closed orientation the access opening of the compartment will be at least partially closed or at least obstructed by interior surface portions of the chamber, thereby preventing inadvertent removal of a needle from the interior of the compartment, through the access opening. Also, the cooperative structuring between the compartment and the interior of the chamber is such as to effectively segregate and/or isolate a needle disposed within the compartment from the interior surfaces of the chamber.

Therefore, the structural and operative features of the packaging and dispensing assembly as noted herein facilitate the initial storage, transportation, and handling of the contained needle in a sterile environment, while the housing and one or more containment structures are in the closed orientation. However, upon reaching its intended destination of use, the one or more containment structures may be selectively disposed into the open orientation, thereby providing convenient access to the needle contained within the compartment of the corresponding retaining segment.

The housing of the present invention further includes a closure structured to removably secure the base and the needle retaining segment of the one or more containment structures in the closed orientation. In at least one embodiment, the closure includes a first closure segment and a second closure segment, each considered a part of the housing and each connected to and movable with a different one of the base and the needle retaining segment. One or more embodiments of the present invention may further define the closure, and more specifically, each of the first and second closure segments as a flange extending outwardly from a corresponding one of the base and needle retaining segment. The flanges are removably secured in confronting relation to one another concurrent to the one or more containment structures being in the closed orientation. Additional structural features of the closure include the ability to repeatedly position the base and retaining segment of each of the one or more containment structures into and out of both the closed orientation and the open orientation.

Therefore, the assembly or structure of the present invention is also capable of facilitating safe disposal of the needle subsequent to its use. In more specific terms, after use the needle is reinserted within the interior of the compartment, through the access opening. The retaining segment and compartment with the needle contained therein, is then selectively positioned from the open orientation into the closed orientation. In order to assure safe and reliable disposal of the needle, the intended design and structuring of the closure will maintain the base and retaining segment, of each of the one or more containment structures, in the closed orientation, absent an appropriately sufficient force to separate the base and the needle retaining segment. Once in the closed orientation, the entire housing and the one or more containment structures, as well as the used needles, may be appropriately discarded.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
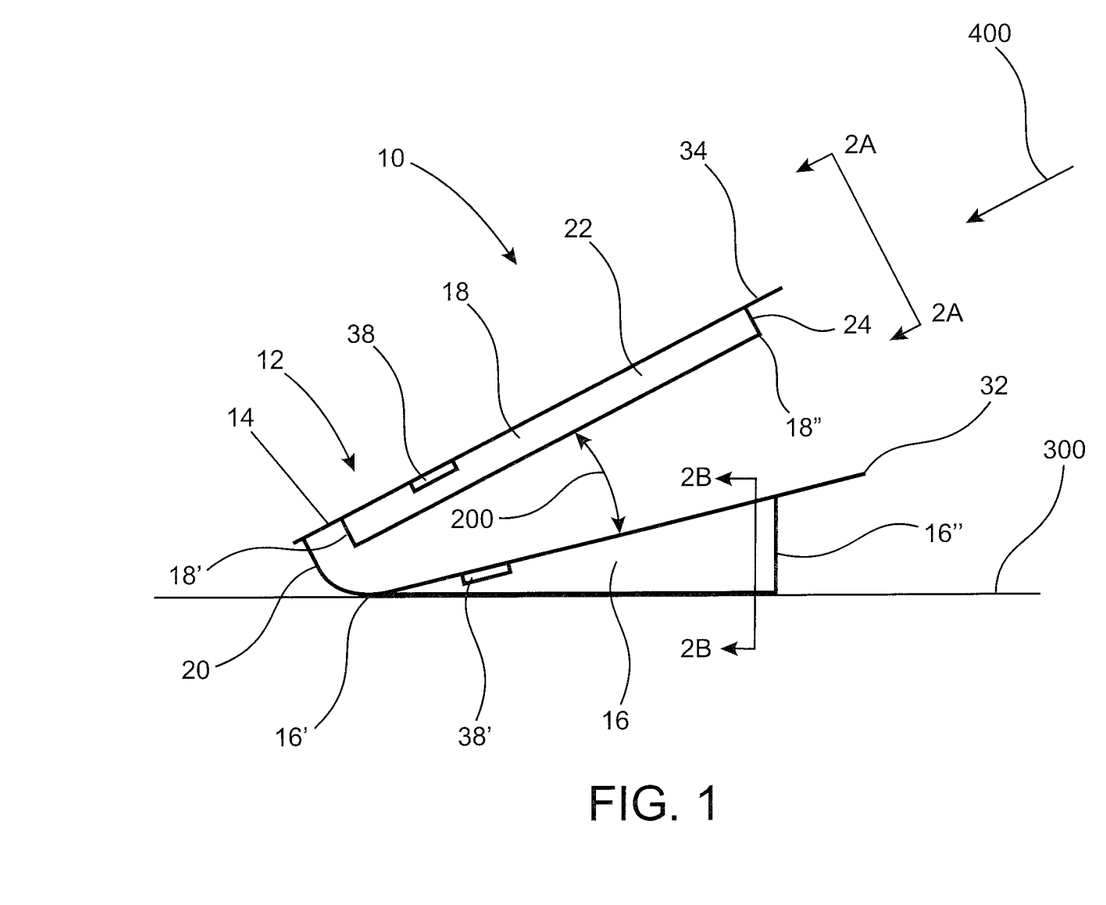
FIG. 1 is a side view of the packaging and disposal assembly of the present invention in an open orientation.
Figure 4:
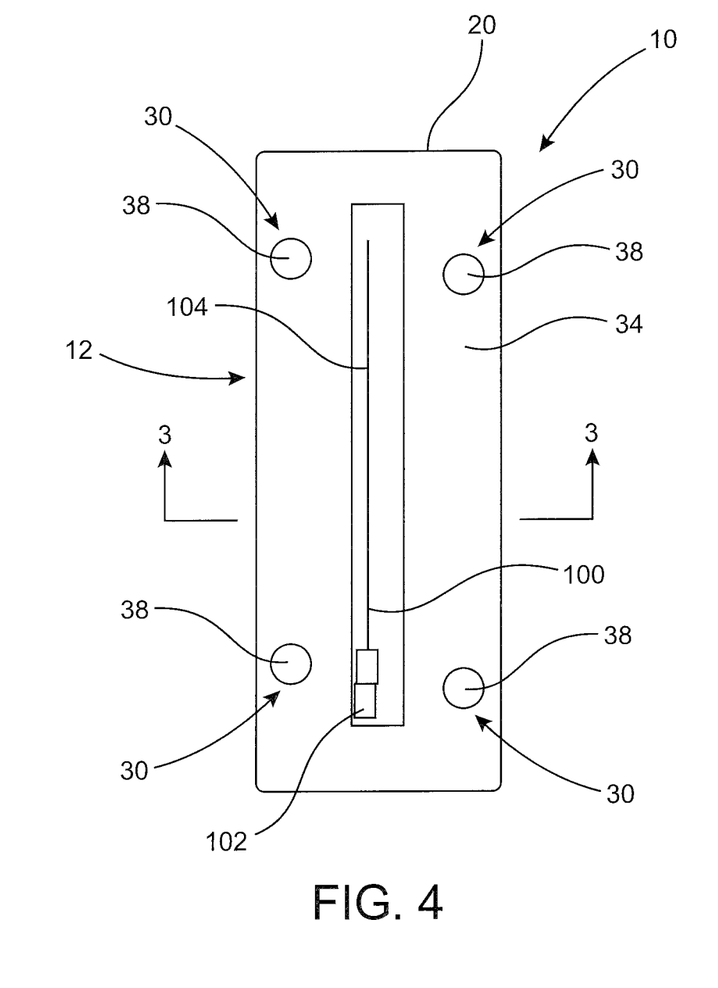
FIG. 4 is a top plan view of the embodiment of FIG. 1 in a closed orientation including a needle contained therein.

As shown in FIG. 1, the present invention is directed to a package and disposal assembly or structure generally indicated as 10 for a needle structure 100 (see also FIG. 4). The needle structure 100 can be, but is not limited to, a medical needle of the type which may be associated with a syringe or other type of medical instrument, container or device. Also, minor structural modifications of the assembly 10 may be made and still fall within the intended scope of the present invention to accommodate needle structures 100, which may vary in type and dimensions. In addition, the operative structuring of the package and disposal assembly 10 facilitates the safe discarding of the needle 100, subsequent to its use. As set forth in greater detail hereinafter, other advantageous features of the present invention include the disposition of the contained needle in a position which facilitates repeated or singular access thereto, when the needle 100 is being utilized.

In more specific terms, the assembly or structure 10 of the present invention comprises a housing generally indicated as 12 including at least one containment structure 14, as represented in FIGS. 1-4. However, and as explained in greater detail herein, the housing 12 may comprise a plurality of such containment structures 14, which would be generally attached to one another in laterally adjacent or contiguous, side-by-side relation. Each of the one or more containment structures 14 is dimensioned and configured to removably contain a needle 100, as explained in greater detail with reference to FIG. 4. Further, each of the one or more containment structures 14 comprises a base 16 and a needle retaining segment 18 movably connected to one another by a hinge 20. The hinge 20 is integrally or fixedly attached to a correspondingly positioned longitudinal ends 16' and 18' of the base 16 and retaining segment 18, thereby at least partially defining a substantially clamshell configuration of the housing 12. As such, the hinge 20 is oriented in substantially perpendicular or at least transverse relation to the length or longitudinal axis of the containment structure 14, specifically including cooperatively positioned ones of the base 16 and retaining segment 18. The hinge 20 is disposed and structured to facilitate selective positioning of the base 16 and retaining segment 18 into and between a closed orientation and an open orientation, respectively represented in FIGS. 3 and 1.

In at least one additional embodiment, wherein the housing 12 includes a plurality of containment structures 14 (not shown), the aforementioned hinge 20 may be common to each of the containment structures 14. In the alternative, a plurality of operatively independent hinges or hinge segments (not shown for purposes of clarity) may be structured and associated with different ones of each of the plurality of containment structures 14. Moreover, in each of the structurally modified embodiments of the hinge and/or hinge segments, the base 16 and the retaining segment 18 of each containment structure 14 may be independently or concurrently disposed in and between the closed orientation and the open orientation.

As indicated, the hinge 20 may be integrally or otherwise fixedly secured to corresponding longitudinal ends 16' and 18' of the base 16 and retaining segment 18. Accordingly, the hinge 20 may be more specifically defined as, but not limited to, a "living hinge" formed of the same or other appropriate material from which the housing 12 and one or more containment structures 14 are formed. This may be a plastic material although in one embodiment of the packaging and disposing assembly 10, the invention may be formed from a polyethylene terephthalate glycol-modified plastic (PETG) material which is produced by the copolymerization of polyethylene terephthalate (PET).

Advantages of using a living hinge include its ability to be continuously and repeatedly bent and/or flexed without breaking, deterioration or damage, due at least in part the existence of minimal friction, within the living hinge, during the operative flexing thereof. Therefore, recognized advantages of the living hinge include quiet operation, low cost and a relative thin and/or flat design requiring minimal space for its intended use and operation. Also, a living hinge may be effectively used in environments where other type hinges may demonstrate wear, corrosion, etc. However, it should be noted that hinge structures and designs, other than a living hinge may be utilized in the movable interconnection of the base 16 and retaining segment 18 of each of the one or more containment structures 14 of the packaging and disposal in assembly 10 of the present invention.

Figure 2A:
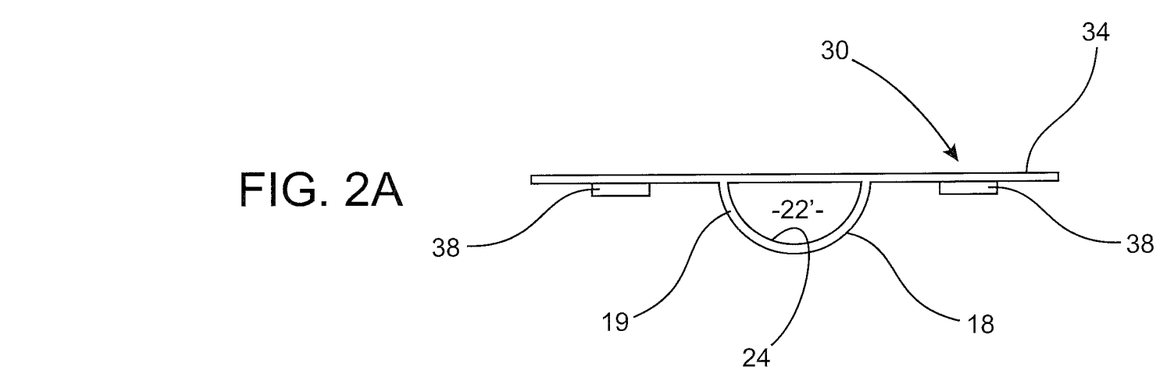
FIG. 2A is an end view along line 2A-2A of the embodiment of FIG. 1.
Figure 2B:
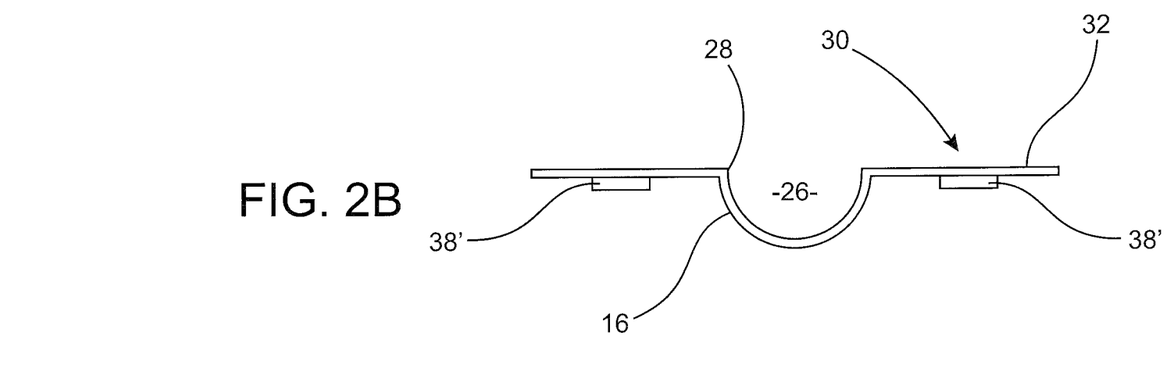
FIG. 2B is a sectional view along line 2B-2B of the embodiment of FIG. 1.

Yet additional structural details of the present invention include the needle retaining segment 18 of each of the one or more containment structures 14 comprising an interior compartment 22 dimensioned and configured to retain at least one needle 100 therein. The compartment 22 includes an elongated configuration having a hollow interior 22' extending along at least a majority of the length thereof and an access opening 24. The access opening 24 is disposed in direct communication with the hollow interior 22'. Further, the access opening 24 is formed on and at least partially defines a longitudinal end 18" of the compartment 22 and is further disposed in substantially opposing relation to the aforementioned hinge 20. As represented in FIG. 2A, the retaining segment 18 includes a substantially closed configuration extending along its length from the access opening 24 to the end 18'. Such a closed configuration is at least partially defined by the side wall 19 of the retaining segment 18 disposed in surrounding relation to and defining the borders of the interior 22' compartment 22.

When the base 16 and retaining segment 18 of the one or more containment structures 14 are disposed in the aforementioned open orientation of FIG. 1, the access opening 24, as well as the needle 100 contained within the corresponding compartment 22, is readily accessible and removable from the compartment 22 via the access opening 24. Accordingly, accessibility to the contained needle 100 within the compartment 22 is yet another feature of the packaging and dispensing assembly 10 of the present invention. Such accessibility is further enhanced by the structuring of the corresponding hinge 20 to maintain a predetermined angular orientation, schematically represented as 200 in at least FIG. 1, of the retaining segment 18 disposed, upwardly and outwardly from the base 16 of the same containment structure 14. Moreover, a preferred predetermined angular orientation 200 of the retaining segment 18, compartment 22 and contained needle 100, relative to the base 16, may be defined as an acute angle. As practically utilized, the base 16 of a given containment structure 14, when in the open orientation of FIG. 1, may be disposed on a substantially horizontal supporting surface 300. In cooperation therewith, the retaining segment 18, compartment 22 and contained needle 100 will be disposed outwardly and/or upwardly from the base 16 into the aforementioned predetermined angle 200 such as, but not limited to an acute angle.

As used herein, the needle or needle structure 100 may be in the form of a medical needle of the type connected to a syringe or other medical instrument, container, etc. As such the needle 100 may include an attachment structure or "hub" 102 secured to one end thereof as represented in FIG. 4. Therefore, when utilized the hub 102, will commonly have a larger or bulkier dimension and configuration than that of the elongated potentially penetrating portion 104 of the needle 100. As a result of such a larger configuration and/or dimension, when the needle 100 is in use, the hub 102 may be positioned to extend at least partially outward from the access opening 24 and thereby be removably retained in such an exposed position, exteriorly of the access opening 24 and compartment 22. As a result, the exposed positioning of the hub 102 facilitates access to and removal of the needle 100 from the interior of the compartment 22, when the containment structure 14 is in the open orientation of FIG. 1, Therefore, the structuring of the hinge 20 associated with a given containment structure 14 is intended to normally bias the retaining segment 18 into the predetermined angular relation 200 relative to the base 16, to at least partially define the open orientation of FIG. 1. It is also to be noted that such a predetermined angular orientation 200 of the retaining segment 18, outwardly from the corresponding base 16, will be substantially maintained, whether the needle 100 remains in the compartment 22 or is removed therefrom through the corresponding access opening 24. As will be explained in greater detail hereinafter, such a preferred, predetermined angular disposition 200 of the retaining segment 18 and the needle 100 removably retained within the compartment 22 serves to position the needle 100 for easy individual and/or repeated access during the utilization of the needle 100 in the intended manner.

Yet additional features of the packaging and disposal assembly of the present invention includes the base 16 comprising a chamber 26 having a hollow interior extending along at least a majority of the length of the base 16 from a closed front end 16" to the opposite end 16', adjacent the hinge 20. The chamber 26 includes an open, inner longitudinal side 28 extending along at least a majority of the length of the base 16. The open inner, longitudinal side 28 is disposed, dimensioned and configured to receive the compartment 22 of the needle retaining segment 18 therein concurrent to a closed orientation. As such, the length as well as the interior dimension of the chamber 26 is sufficient to enclose the compartment 22 of the corresponding retaining segment 18, concurrent to the compartment 22 passing through the open longitudinal side 28 of the chamber 26 as the containment structure 14 moves into the closed orientation.

Figure 3:
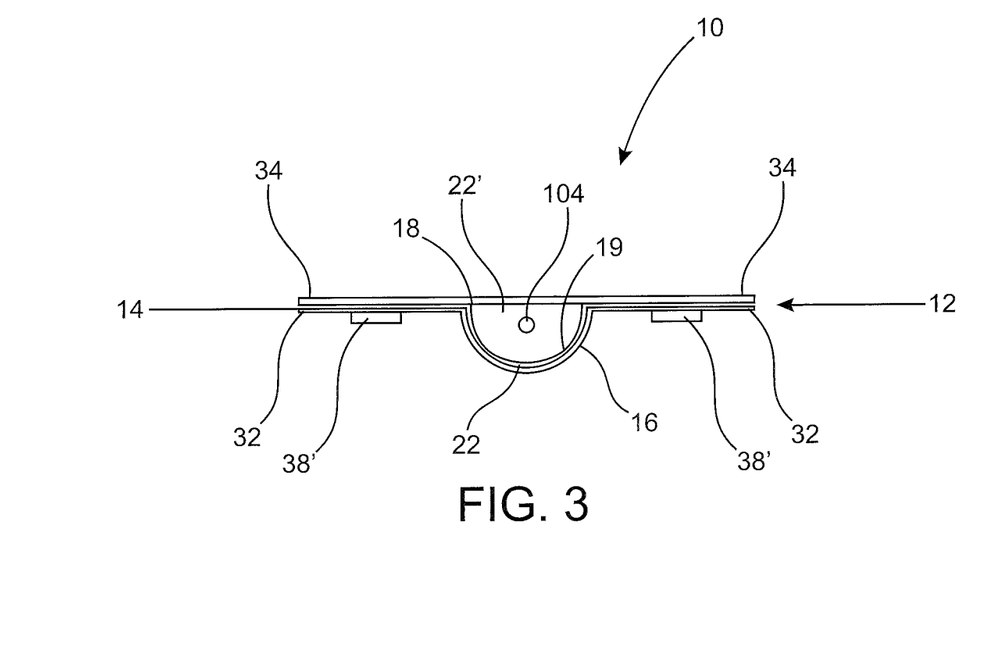
FIG. 3 is a sectional view along line 3-3 of the embodiment of FIG. 4.

Further, the length as well as the interior dimension of the chamber 26 is sufficient to enclose the compartment 22 of the corresponding retaining segment 18, concurrent to the containment structure 14 being in the aforementioned closed orientation, as represented in FIGS. 3 and 4. Moreover, when in the closed orientation, the access opening 24 will be at least partially closed or at least obstructed by interior surface of the closed end 16" of the base 16. The closing or blocking of the access opening 24 by the closed end 16" will prevent inadvertent removal of a contained needle 100 from the interior of the compartment 22, through the access opening 24, when the containment structure 14 is in the closed orientation. Also, the cooperative structuring between the compartment 22 and the interior of the chamber 26 is such as to effectively enclose at least a majority and in some embodiments an entirety of the compartment 22, as also represented in FIG. 4. Further, the enclosed disposition of the chamber 22 within the interior of the chamber 26 will result in a segregated positioning of the needle 100 from interior surface portions of the chamber 26, due at least in part to the closed configuration of the chamber 22 by the surrounding, enclosing side wall 19, as set forth herein.

Therefore, the structural and operative features of the packaging and dispensing assembly 10, as noted herein, facilitate the initial storage, transportation, and handling of the contained needle 100 in a sterile environment, while the housing 12 and the one or more containment structures 14 associated therewith are in the closed orientation. However, upon reaching its intended destination of use, the one or more containment structures 14 may be selectively disposed into the open orientation of FIG. 1, thereby providing convenient and facilitated access to the needle 100 within the compartment 22 of the corresponding retaining segment 18.

The housing 12 of the present invention further includes a closure, generally indicated as 30, structured to removably but securely maintain the base 16 and the needle retaining segment 18 of the one or more containment structures 14 in the closed orientation. In at least one embodiment, the closure 30 includes a first closure segment 32 and a second closure segment 34 each connected to and movable with a different portion of the housing 12, respectively connected to the base 16 and the needle retaining segment 18. Therefore, one or more embodiments of the present invention may further define the closure 30 and more specifically, the first and second closure segments 32 and 34 as a flange respectively extending outwardly from a corresponding one of the base 16 and needle retaining segment 18. In addition, the closure 30 includes at least one, but more practically, a plurality of pairs of cooperatively structured closure members 38 and 38', which are respectively formed in the closure segment flanges 32 and 34.

More specifically, one embodiment of the present invention includes the closure 30 comprising each of the one or more pairs of closure members 38, 38' comprising a protruding member 38 integrally formed in one of the flanges, such as at 34. In turn, closure member 38' may be a recess structure integrally formed in closure segment flange 32 and disposed and configured to removably receive the protruding member 38 therein. The at least minimal flexibility of the plastic material from which the closure members 38, 38' are formed facilitate a removable, snap-type connection therebetween. Further, the cooperative dimensioning between the closure members 38, 38' serve to maintain their attachment and in turn maintain the closed orientation of the containment structure 14, until a sufficient force is exerted on the base 16 and/or needle retaining segment 18 sufficient to cause a separation thereof into the open orientation. As also indicated herein, such a "sufficient force" should be such as to prevent or restrict the possibility of inadvertent separation of the base 16 and retaining segment 18 when in the closed orientation, in order to assure safe disposal of the needle 100 subsequent to use.

Accordingly, as represented in FIG. 3, the closure segment flanges 32 and 34 are removably secured in confronting relation to one another concurrent to the one or more containment structures 14 being in the closed orientation. Additional structural features of the closure 30, including the at least one pair of closure members 38 and 38', include its ability to repeatedly position corresponding ones of the base 16 and retaining segment 18 of each of the one or more containment structures 14 into and out of both the closed orientation of FIG. 3 and the open orientation of FIG. 1.

Therefore, the packaging and disposal assembly or structure 10 of the present invention is capable of facilitating safe disposal of the needle 100 subsequent to its use. More specifically, after use, the needle 100 is disposed within the interior of the compartment 22, through the access opening 24 as represented by directional arrow 400. The retaining segment 18 and compartment 22, with the needle 100 contained therein, is then selectively positioned from the open orientation into the closed orientation. The structuring of the of the closure assembly 30 including the one or more pair of closure members 38, 38', will maintain the base 16 and retaining segment 18 of each of the one or more containment structures 14 in the closed orientation of FIG. 3. Once in the closed orientation, the entire housing 12, the one or more containment structures 14 as well as subsequently used one or more needles 100 may be appropriately discarded. In order to assure safe and reliable disposal, the aforementioned closure 30 is specifically structured to maintain the housing and containment structure in the closed orientation until a "sufficient force" is applied to the housing 12, in the manner at least generally set forth above.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An assembly for packaging and disposing of a needle structure, said assembly comprising:
a housing including at least one containment structure dimensioned and configured to contain a needle therein,
said at least one containment structure comprising a base and a needle retaining segment,
a hinge attached to and movably interconnecting said base and said needle retaining segment between a closed orientation and an open orientation,
said needle retaining segment comprising a compartment dimensioned and structured to removably retain the needle therein, concurrent to said open orientation,
said compartment comprising a closed configuration at least partially defined by a side wall disposed in surrounding, enclosing relation to an interior of said compartment,
said hinge including a biased construction structured to normally bias said housing in said open orientation,
said open orientation comprising said needle retaining segment separated from said base and extending outwardly therefrom in a predetermined angular relation thereto,
said base comprising a chamber formed therein; said closed orientation at least partially defined by said compartment disposed within said chamber, and
said chamber is dimensioned and configured to enclose at least a majority of said compartment and the needle contained within said compartment, concurrent to said closed orientation.

2. The assembly as recited in claim 1 wherein said predetermined angular relation comprises said needle retaining segment disposed outwardly from and connected to said base at an acute angle.

3. The assembly as recited in claim 1 wherein said hinge comprises a living hinge integrally connected to said base and said needle retaining segment.

4. An assembly as recited in claim 1 wherein said hinge is disposed at one end of said housing, and extending in transverse relation to a length of said base and said needle retaining segment.

5. The assembly as recited in claim 4 wherein said needle retaining segment comprises a compartment including an access opening disposed at one end thereof opposite to said hinge.

6. The assembly as recited in claim 1 wherein said compartment is disposed and structured to segregate the needle disposed therein, from an interior of said chamber, concurrent to said closed orientation.

7. The assembly as recited in claim 1 wherein said housing comprises, a closure structured to removably secure said base and said needle retaining segment in said closed orientation; said closure comprising a first closure segment and a second closure segment respectively connected to and movable with said base and said needle retaining segment.

8. The assembly as recited in claim 7 wherein each of said first and second closure segments comprises a flange extending outwardly from a corresponding one of said base and said needle retaining segment; said flanges removably secured in confronting relation to one another, concurrent to said closed orientation.

9. An assembly for packaging and disposing of a needle structure, said assembly comprising:
a housing including at least one containment structure dimensioned and configured to contain a needle therein,
said at least one containment structure comprising a base and a needle retaining segment,
said housing including a hinge movably interconnecting said base and said needle retaining segment between a closed orientation and an open orientation,
said needle retaining segment comprising a compartment dimensioned and structured to removably contain the needle therein, said compartment comprising a closed configuration defined by a side wall disposed in surrounding, enclosing relation to an interior of said compartment, said base comprising a chamber formed therein; said closed orientation comprising said compartment enclosed in its entirety within said chamber, said hinge having a biased construction, extending transversely to a length of said housing, and structured to normally bias said housing in said open orientation, and said open orientation comprising at least a majority of a length of said needle retaining segment and said compartment disposed in outwardly spaced relation from one another in a needle accessible, predetermined angular orientation.

10. The assembly as recited in claim 9 wherein said predetermined angular relation comprises said needle retaining segment and said compartment disposed outwardly from said base at an acute angle.

11. The assembly as recited in claim 9 wherein said compartment comprises an access opening defined by an open end thereof disposed opposite to said hinge; said access opening dimensioned to allow passage therethrough into and out od said compartment.

12. The assembly as recited in claim 9 wherein said compartment is disposed and structured to segregate the needle disposed therein, from an interior of said chamber, concurrent to said closed orientation.

13. The assembly as recited in claim 9 further comprising a closure structured to removably secure said housing in said closed orientation; said closure comprising a first closure segment and a second closure segment each fixedly connected and movable with a different one of said base and said needle retaining segment.

14. The assembly as recited in claim 13 wherein each of said first and second closure segments comprises a flange extending outwardly from a corresponding one of said base and said needle retaining segment; at least two closure members each disposed on a different one of said flanges; said at least two closure members cooperatively disposed and structured to removably secure said flanges in confronting relation to one another, concurrent to said closed orientation.

15. The assembly as recited in claim 9 wherein said hinge is disposed at one end of said housing, in transverse relation to a length of said at least one containment structure.

* * * * *